United States Patent [19]
Steele et al.

[11] Patent Number: 5,416,002
[45] Date of Patent: May 16, 1995

[54] NEAR-REAL-TIME MICROBIAL MONITOR

[75] Inventors: John W. Steele, Torrington; W. Clark Dean, Simsbury, both of Conn.

[73] Assignee: United Technologies Corporation, Windsor Locks, Conn.

[21] Appl. No.: 984,750

[22] Filed: Dec. 3, 1992

[51] Int. Cl.[6] .................. G01N 21/76; C12Q 1/66
[52] U.S. Cl. ........................... 435/8; 435/29; 435/30; 435/31; 435/291; 435/311; 422/52; 422/101; 436/172
[58] Field of Search .............. 422/52, 101; 435/8, 435/29, 291, 30, 311, 31; 436/172

[56] References Cited
U.S. PATENT DOCUMENTS

| | | | |
|---|---|---|---|
| 3,754,868 | 8/1973 | Witz et al. | 422/52 |
| 3,940,250 | 2/1976 | Plakas et al. | 435/8 |
| 3,979,181 | 9/1976 | Plakas | 422/52 |
| 4,013,418 | 3/1977 | Plakas | 422/52 |
| 4,144,134 | 3/1979 | Plakas | 435/8 |
| 4,385,113 | 5/1983 | Chappelle et al. | 435/8 |
| 4,672,039 | 6/1987 | Lundblom | 422/52 |
| 5,141,869 | 8/1992 | Steele et al. | 435/291 |

*Primary Examiner*—James C. Housel
*Assistant Examiner*—Jan M. Ludlow

[57] ABSTRACT

The use of bioluminescence on a filtration enrichment sample and a light measuring device allows microbial monitoring in liquids without sample incubation. All characteristics of this monitor are zero gravity compatible which makes it particularly suitable for applications such as monitoring microbial counts in water in a zero gravity, closed environment.

10 Claims, 3 Drawing Sheets

NEAR-REAL-TIME MICROBIAL MONITOR

TECHNICAL FIELD

The present invention relates to a method and apparatus for analyzing microorganisms in liquids, and more particularly to a liquid microbial analysis which is independent of growth media and requires no incubation and can be analyzed by a bioluminescence microbial monitor.

BACKGROUND OF THE INVENTION

The analysis of microorganisms in a liquid, such as water, milk, or soft drinks for human consumption and water for microelectronic and pharmaceutical product processing is of the utmost importance to health and product integrity, respectively. Microbial count analysis typically consists of a labor intensive manual membrane filtration followed by a 48 to 72 hour incubation period. Several different growth media and incubation temperatures are often necessary to get a full microbial profile of a particular liquid.

The results of the microbial analysis are interpreted by a trained analyst who visually counts the number of colonies on the filter paper after incubation. Each colony represents a single colony forming unit (CFU) in the initial sample. From this information, the number of CFUs per unit volume is determined.

The long lag times of 48 to 72 hours required for a microbial analysis frequently lead to product waste in the microprocessor and pharmaceutical industries since a failure requires that products already produced, have to be discarded. A chronic microbial contamination situation can lead to 48-72 hours worth of discarded products before testing alerts the user to the unacceptable situation.

Further, the capability for microbial monitoring of processed liquid for human consumption is necessary for health and welfare. Membrane filtration, as previously stated, is labor intensive, is not selective to all potentially present microbes as a single test, and required 48-72 hours of incubation time prior to acquiring results. With a 48-72 hour lag time before results, for example, a space station user is faced with the dilemma of deciding whether the test results of a 2-3 day old sample are still representative of the actual water source.

Bioluminescence has been utilized by both the food industry and medical field to detect high concentrations of microbes. The detection process consists of measuring adenosine triphosphate (ATP); a nucleotide found in all living cells. ATP, the primary energy donor in viable cells, rapidly degrades as the cell dies. With the use of the enzyme luciferase (see U.S. Pat. No. 4,833,075), ATP can be measured.

ATP is released from living bacterial cells with the use of a bacterial release agent which lyses microbial cell walls. In the presence of oxygen ($O_2$), magnesium ($Mg^{++}$) and luciferase, ATP drives the conversion of luciferin to oxyluciferin. This reaction results in the conversion of ATP to adenosine monophosphate (AMP) and the release of a photon of light.

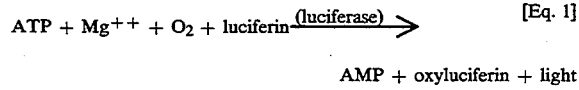

[Eq. 1]

The light can be measured by a luminometer if the concentration of microbes is about 80-100 CFU absolute or greater, the current sensitivity for the state of the art. Note, bioluminescence is typically utilized for grossly concentrated samples, not for trace level analysis.

This process is typically accomplished by sequentially adding a bacterial release agent, luciferin/luciferase, and $Mg^{++}$ to a liquid sample while a fixed luminometer records any offsets due to emitted light from the sample.

At present, bioluminescence is used to monitor growth enriched samples of filtered liquids. For example, U.S. Pat. No. 5,141,869 is directed to a microbial monitor having a bladder for growth enrichment of microbial concentrations in a liquid sample with a growth buffer and incubation for enriching the amount of microbes in the liquid sample.

Each of the above discussed analysis of microorganisms in liquids requires a complicated sampling system requiring long periods of time to incubate a sample, e.g. in an incubator and using a growth buffer, prior to count analysis.

SUMMARY OF THE INVENTION

Accordingly, it is an object of the present invention to provide a microbial analysis process and monitor that offers a simplified and near-real time solution to the analysis of microorganisms in liquids which can be utilized in zero gravity environments.

The present invention relates to a near-real-time bioluminescence microbial monitor and a process for using the same. The microbial monitor is comprised of a sample collection and filtration enrichment assembly, a luminescence package comprising a dried luciferin/luciferase reagent releasably separatable from a bacteria release agent, a mixing means, e.g. a pump/motor package, for mixing the dried luciferin/luciferase reagent, ATP release agent, and a concentration of microbes collected in the filtration enrichment assembly, and a means for measuring emitted light. The process includes grabbing a liquid sample which has been introduced to a peristaltic collection and filtration assembly, inserting the collection and filtration assembly with its sample into a luminescence package, combining the luciferin/luciferase and bacteria release agents, and measuring the light emitted.

The foregoing and other features and advantages of the present invention will become more apparent from the following description and accompanying drawing.

BEST MODE FOR CARRYING OUT THE INVENTION

This invention can be used to detect microbes, such as bacteria, in any liquid which does not degrade the detector or the chemicals used and which does not contain any other living cells such as somatic cells. The filtering process, with the use of a 10 liter sample, allows microbe concentration sensitivity of 1 CFU/100 cc.

Figure 1:
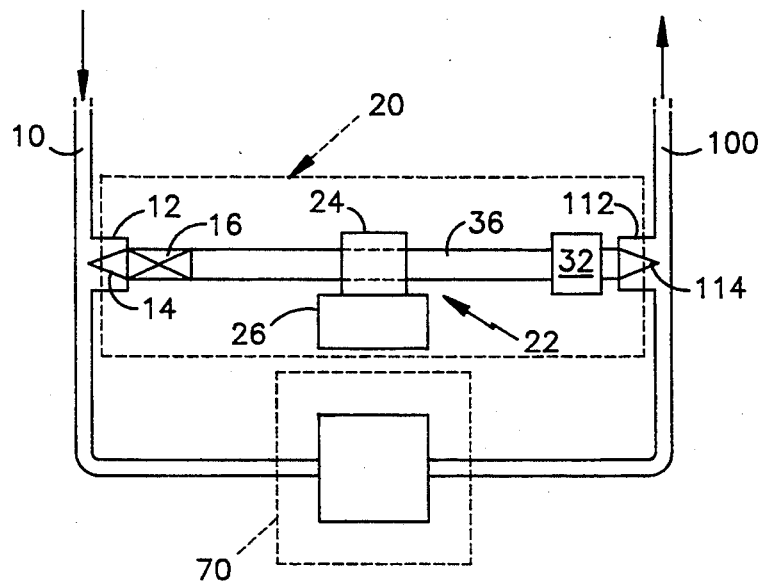
FIG. 1 is a schematic diagram of an embodiment of the collection and filtration assembly and the pump/motor package apparatus of the present invention.

Referring to FIG. 1, which is intended to be exemplary and not limiting, the microbial collection and filtration apparatus 20 of the present invention is connected to a liquid supply line 10 and a liquid return line 100 which normally feeds a liquid process, e.g. potable water system 70. The collection and filtration apparatus 20 comprises an inlet needle means 14 and an outlet needle means 114, a valve 16, connecting tubing 36, filter element 32, and pump assembly 22 having a pump means 24 and a motor means 26.

The connecting tubing 36 useful for zero gravity operation may comprise a flexible tube for moving a sample therethrough using the pump assembly, e.g. a pump having an action suggestive of peristalsis in connection with the flexible tube. The capacity of the connecting tube 36 is determined by the amount of bacterial release agent and dried luciferin/luciferase in the bioluminescence package described hereinafter. Moreover, the capacity of the connecting tube 36 is in direct relation to the volume of the supplied bacteria release agent and dried Luciferin and Luciferase. Preferably, the capacity of the connecting tubing 36 is 3 cc. Accordingly, the volume of the supplied amount of bacteria release agent and Luciferin/Luciferase would also be 3 cc because of the above identified direct relation.

The bacteria filter 32 is used as a filtration enrichment means for the liquid sample. The bacteria filter 32, which can be any filter commonly known in the art, must have a pore size small enough to trap the microbes yet large enough to allow liquid permeation. Since a typical microbe ranges in size from about 0.50 to about 1.0 microns, a pore size less than about 0.50 microns can be used. Preferably, the pore size is 0.2 micron. The filter should be surrounded by a clear housing to permit light therethrough. For example, the housing may be Lexan®.

The collection and filtration process consists of passing sufficient liquid through the connecting tubing 36 and filter element 32 in the collection and filtration apparatus 20. The liquid is passed through the bacteria filter 32 to allow for filtration enrichment.

Once the liquid sample has been filtration enriched, the pump assembly 22 is stopped and valve 16 is closed. The pump means 24 is then rotated, e.g. manually or electrically, to remove all but about 1 cc of water sample from the connecting tube 16, whereupon the collection and filtration apparatus 20 is disconnected from the sample ports 12, 112 and connected to a bioluminescence monitoring apparatus as shown in FIG. 2.

Figure 2:
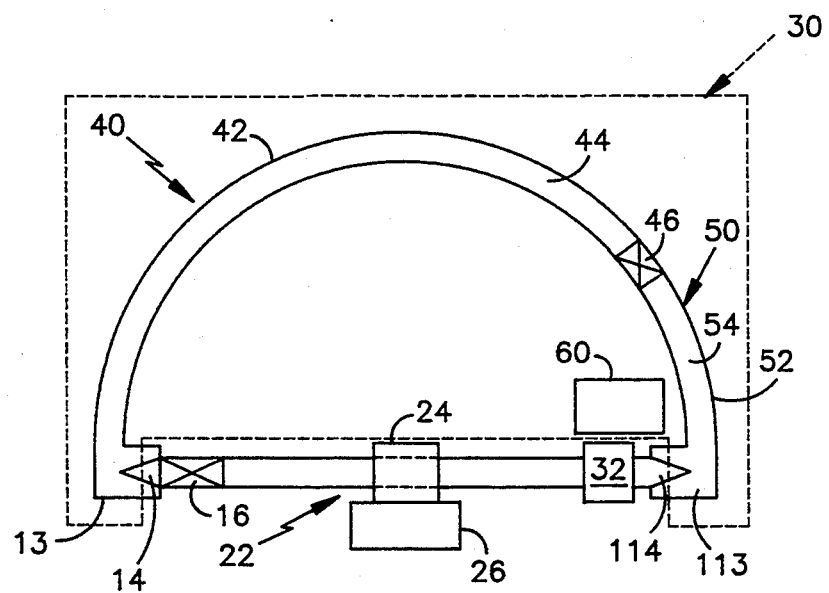
FIG. 2 is a schematic diagram of one possible embodiment of the bioluminescence monitoring apparatus of the present invention.

Referring now to FIG. 2, which is intended to be exemplary and not limiting, the collection and filtration apparatus 20 containing the enriched sample is further connected to the microbial monitor 30 of the present invention which contains a bacteria release agent means 40, a luciferin/luciferase means 50, and a means for measuring emitted light 60.

The microbial monitor 30 has a container element 42, preferably a flexible tube, containing bacteria release agent 44, which is releaseably separatable by separation means 46, e.g. a clip squeezable about the flexible tube 42, from a second container element 52, which can be a portion of the flexible tube 42, containing luciferin/luciferase 54, preferably freeze dried. The microbial monitor 30 has inlet port 13 and outlet port 113 for connection to the inlet and outlet needle means 14, 114 of the collection and filtration apparatus 20.

The luciferin/luciferase can be obtained from Los Alamos Diagnostics Inc., Los Alamos, N. Mex. in a premixed, freeze dried form. It is also possible to purchase luciferin and luciferase separately and combine them at a ratio which can readily be determined by an artisan.

The bacteria release agent can be any enzyme mix or extracting reagent which lyses cells to release cellular ATP and inhibits enzymatic activity in the extract, such as Picoex B ™ produced by Los Alamos Diagnostics Inc., Los Alamos, N. Mex.

To prevent contact between the luciferin/luciferase and the bacteria release agent before intended use, the separation means 46 is used.

Once the collection and filtration apparatus 20, containing the enriched sample, is connected to the microbial monitor 30, the separation means 46 is opened, the valve 16 is opened, the filter element 32 is placed in proximity to the light measuring means 60, and the pump 24 is started to mix the components for about 5 seconds followed by light readings.

Light readings are taken until the reaction has gone to completion, typically approximately 30 seconds. Any means for measuring light (photons) conventionally known in the art can be utilized, such as a luminometer 60 or photometer. Note, the light can be transferred from the luciferin/luciferase assembly 50 to the luminometer 60 by any means conventionally known in the art which will not contaminate the sample or the light itself, such as fiber optics or a window connected to a tube.

After the analysis is complete, the collection and filtration apparatus 20 and microbial monitor 30 are disassembled, and with the exception of the pump assembly 22 and the light measuring means 60, can be discarded or reclaimed by cleaning, autoclaving, and recharging. Note, all remaining components should be sterilized, such as by heat, prior to subsequent analysis procedures to prevent contamination.

Figure 3:
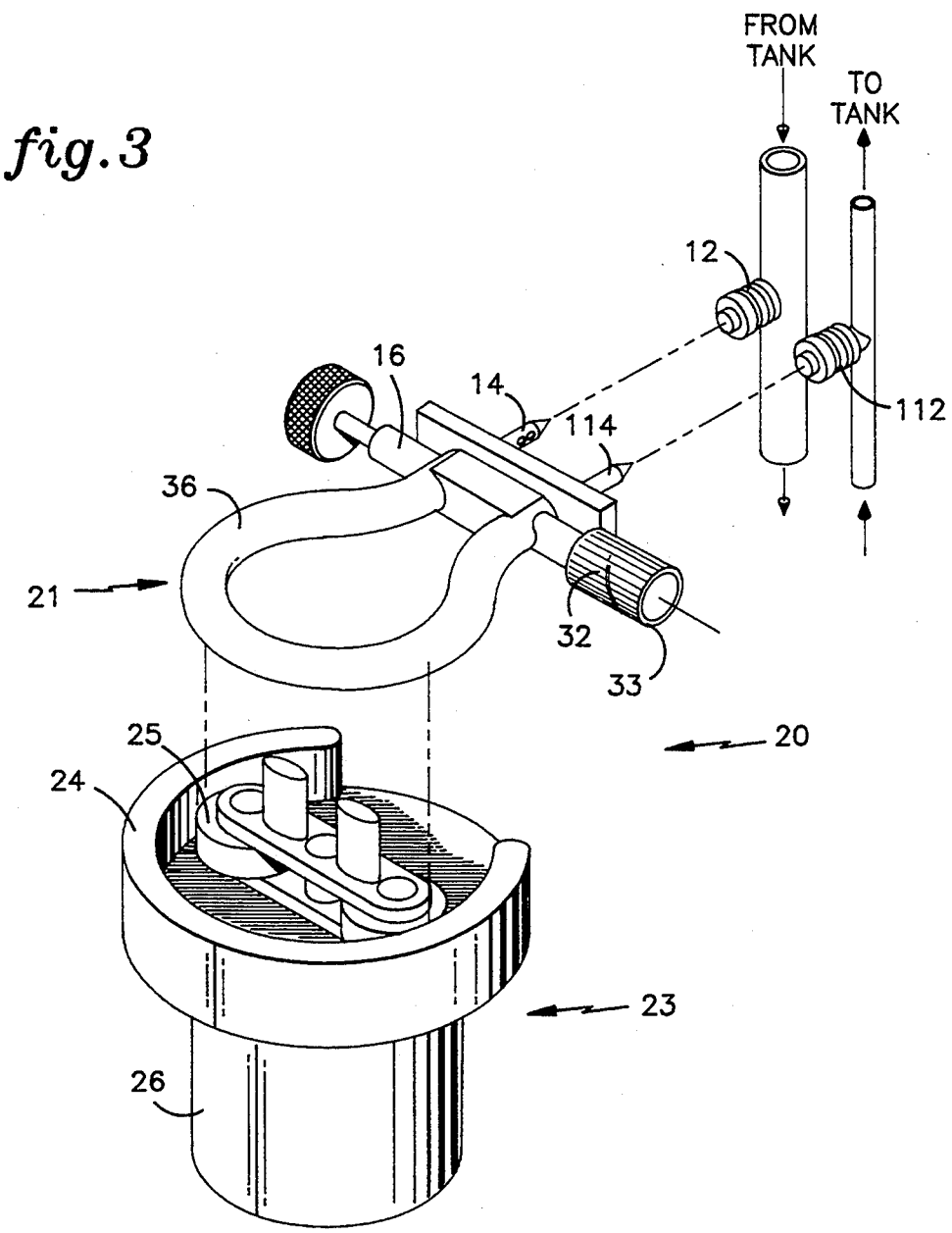
FIG. 3 is a perspective view of an apparatus for collecting and filtering a sample of the present invention.

Referring now to FIG. 3 there is shown an embodiment of the collection and filtration apparatus 20 which preferably contains a pump package subassembly 21 and a pump motor subassembly 23. The pump package subassembly 21, which can be packaged in a protective envelope, contains an inlet needle means 14 and an outlet needle means 114 for connecting to sample ports 12, 112, a valve 16 for providing sample flow through the subassembly, connecting tubing 36 which is preferably a flexible tube or peristaltic pump element with a desired capacity, and a filter element 32 for filtration enrichment of a sample surrounded by a clear housing 33. The pump motor subassembly 23 contains a motor means 26 operated by external electric power connected to a pump means 24, preferably a plurality of rotating roller means 25 for engagement with the connecting tube 36 for moving a liquid sample therethrough.

Figure 4:
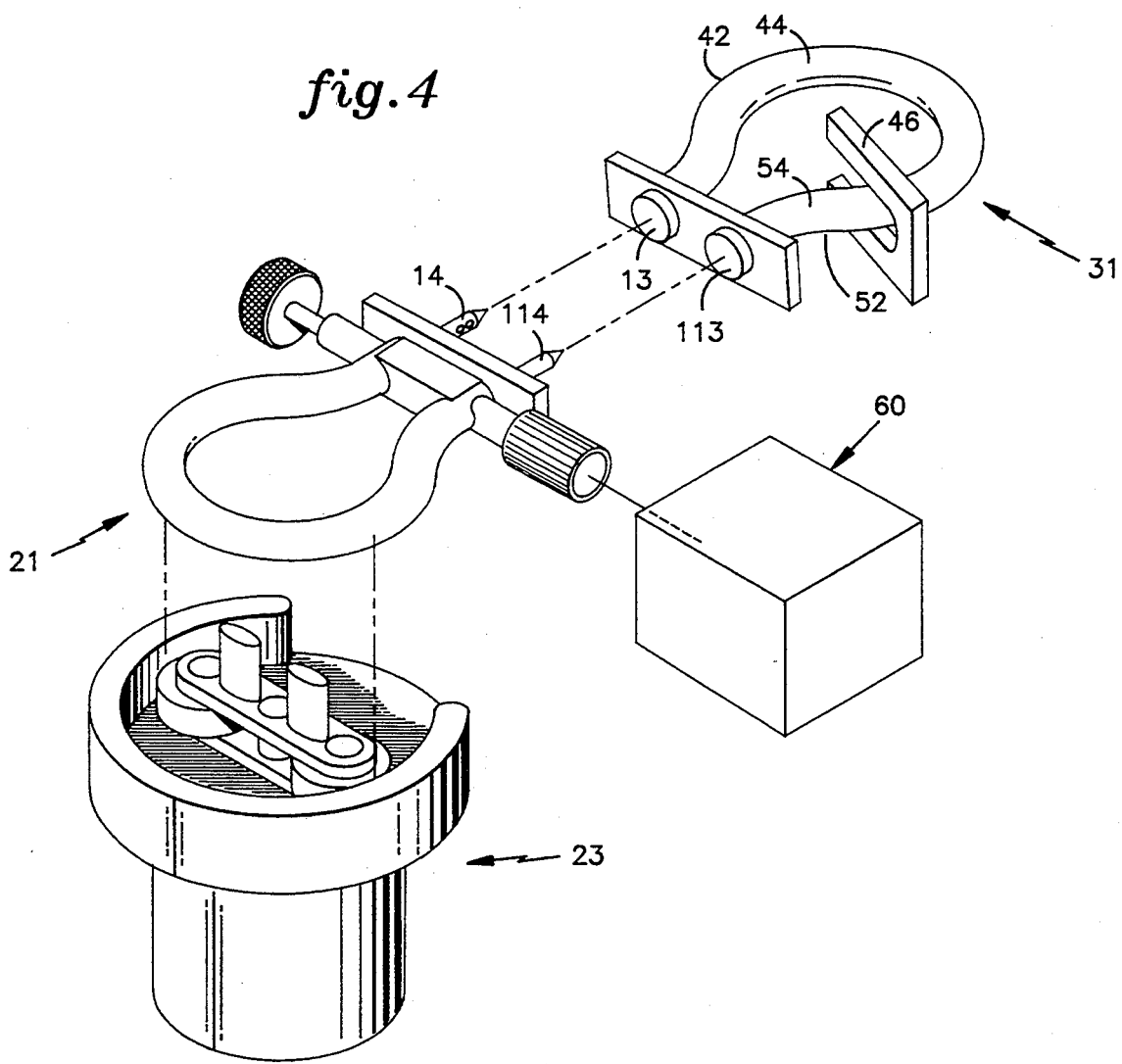
FIG. 4 is a perspective view of a bioluminescence microbial monitoring apparatus of the present invention.

Referring now to FIG. 4, there is shown an embodiment of the bioluminescence microbial monitor which preferably contains the pump package subassembly 21, a bioluminescence subassembly 31, and a means for measuring emitted light 60. The bioluminescence subassembly 31, which can also be packaged in a protective envelope, contains an inlet port 13, an outlet port 113 for connecting to the inlet and outlet needle means 14, 114, a container element 42, preferably a flexible tube having a desired capacity containing a bacteria release agent 44, a second container element 52, preferably a portion of the flexible tube of container element 42 containing a luciferin/luciferase 54, and separation means 46, preferably a clip squeezable about the flexible tube to prevent combining the bacteria release agent and luciferin/luciferase when the subassembly is not being used.

Thus, as shown in FIGS. 3 and 4, the present invention provides an apparatus and method for sample collection and filtration enrichment. This is followed by a zero gravity compatible approach for reagent addition to the sample. Since no sample incubation is required, detected microorganisms are independent of media type and incubation temperature.

EXAMPLE

The following operation can be used to obtain a microbial count in potentially potable water, e.g. in a zero gravity environment.

1. Remove a pump package subassembly 21 from its protective envelope and install in the pump motor subassembly 23.
2. Locate the inlet 12 and outlet 112 sample ports in the system to be tested (one on tank inlet line, one on tank outlet line), then heat sterilize sample ports.
3. Insert the inlet 14 and outlet 114 needle means into the sample ports. Attach the pump motor subassembly to a support bracket, connect the motor to a power outlet and start the motor for a timed pump period.
4. When the motor ends its sample cycling, e.g. an alarm may sound, the user closes the valve 16 and rotates the pump rollers 25 to remove all but 1 cc of water sample from the connecting tubing 36 or the pump package subassembly 21.
5. Remove the pump motor subassembly with the attached pump package subassembly from the sample ports.
6. Remove a bioluminescence subassembly 31 from its protective envelope, and insert the needle means 14, 114 into the inlet 13 and outlet 113 ports of the bioluminescence subassembly 31.
7. Remove the 46 clip from the bioluminescence subassembly 31 and open the valve 16 on the pump package subassembly 21.
8. Insert the filter element 32 into a test chamber on a luminometer 10 while still attached to the pump package subassembly.
9. Start a mix and test cycle. The pump should mix for 5 seconds, followed by 30 seconds of luminometer readings of the light emitted from the filter. Results may then be displayed, e.g. on a digital meter.
10. Remove the subassembly filter element 32 from the luminometer and dispose of the used pump package subassembly and bioluminescence subassembly.

A 10 liter sample should provide the user with 1 CFU/100 cc sensitivity. A near-real-time microbial monitoring device with the capability of providing 1 CFU/100 cc sensitivity generally in less than 1 hour total test time, with generally a 5 minute user interaction time, is thus provided.

Unlike the prior art, the present invention requires minimal microbial analysis know-how from the user, can be operated in zero gravity, and requires no incubation period. There also is no need for specific incubation temperatures or growth media.

Although this invention has been shown and described with respect to detailed embodiments thereof, it will be understood by those skilled in the art that various changes in form and detail thereof may be made without departing from the spirit and scope of the claimed invention.

We claim:

1. A microbial monitor comprising:
   a. A collection assembly defining a first enclosed flow path for a liquid sample;
   b. a bacteria filter located within the first enclosed flow path defined by said collection assembly for concentration on said filter of microbes in said liquid sample;
   c. container means containing luciferin and luciferase releasably separated from an ATP release agent, said container means defining a second enclosed flow path selectively connectable in flow communication with said collection assembly to form a closed flow loop;
   d. a coupling means for selectively coupling said collection assembly to a source of said liquid sample or said container means;
   e. a means for mixing the luciferin and luciferase with the ATP release agent and the concentration of microbes on said bacteria filter within said closed flow loop thereby causing emission of light; and
   f. a means for measuring said emitted light, said measuring means located adjacent said filter.

2. A microbial monitor as in claim 1 wherein said bacteria filter further includes a housing translucent to light.

3. A microbial monitor as in claim 1 wherein said collection assembly is a flexible tube.

4. A microbial monitor as in claims 3 wherein the volume capacity of said flexible tube is generally equal to the volume of said container means.

5. A microbial monitor as in claim 4 wherein said bacteria filter includes a housing translucent to light.

6. A microbial monitor as in claim 5 wherein the luciferin and luciferase is contained in a first portion of said container means and the ATP release agent is contained in a second portion of said container means, and said first and second portions of said container means are separated by a releasable closure means.

7. A microbial monitor as in claims 6 wherein said container means is a second flexible tubing.

8. A process for monitoring microbial count in a liquid sample comprising:
   a. introducing the liquid sample into and transferring the liquid sample through a collection assembly which defines an enclosed flow path for the liquid sample;
   b. filtering the liquid sample through a bacteria filter within the flow path defined by said collection assembly wherein concentration of microbes occurs in said bacteria filter;
   c. connecting the enclosed flow path defined by the collection assembly after the concentration of the microbes occurs to a package means containing a supply of luciferin and luciferase and a supply of ATP release agent wherein said package means defines a second enclosed flow path to form a closed flow loop;

d. connecting said bacteria filter in working relation to a light measuring means;

e. mixing the supply of luciferin and luciferase with the supply of ATP release agent and the concentrated microbes, within said closed flow loop thereby causing the emission of light;

f. measuring the light emitted from said bacteria filter by said light measuring means.

9. A process for monitoring microbial count as in claim 8 wherein the volume of said package means is in direct relation to the capacity of the collection assembly.

10. A zero gravity microbial monitor comprising:

a. A flexible conduit means defining a first enclosed flow path for a liquid sample, said conduit means including a bacteria filter fixedly located within said first enclosed flow path for concentration of microbes in said liquid sample and a flow inducing means for inducing said liquid sample through said first enclosed flow path;

b. a luminescence means for causing luminescence of the collected microbes on said bacteria filter, said luminescence means including a first container portion containing a supply of dry luciferin and luciferase, a second container portion containing a supply of ATP release agent, and a releasable separation means for releasably separating the contents of said first portion from the contents of said second portion, said luminescence means defining a second enclosed flow path;

c. means for selectively coupling said flexible conduit means to a source of liquid sample or said luminescence means;

d. a means for mixing the luciferin and luciferase, the ATP release agent, and the collected microbes on said bacteria filter when said first enclosed flow path is selectively coupled to said second enclosed flow path to form a closed flow loop, thereby causing emission of light, said mixing means being free from contact with the liquid sample or collected microbes in said enclosed flow path; and e. a means for measuring said emitted light, said measuring means located adjacent said filter.

* * * * *